（12） United States Patent
Naka (10) Patent No.: US 10,393,706 B2
(45) Date of Patent: Aug. 27, 2019

(54) MECHANICAL SCANNING 3D ULTRASONIC TRANSDUCER (71) Applicant: NIHON DEMPA KOGYO CO., LTD., Tokyo (JP)

(72) Inventor: Yoji Naka, Saitama (JP)

(73) Assignee: NIHON DEMPA KOGYO CO., LTD., Tokyo (JP)

( * ) Notice: Subject to any disclaimer, the term of this patent is extended or adjusted under 35 U.S.C. 154(b) by 165 days.

(21) Appl. No.: 15/326,494

(22) PCT Filed: Jul. 10, 2015

(86) PCT No.: PCT/JP2015/069842
§ 371 (c)(1),
(2) Date: Jan. 15, 2017

(87) PCT Pub. No.: WO2016/009953
PCT Pub. Date: Jan. 21, 2016

(65) Prior Publication Data
US 2018/0209944 A1 Jul. 26, 2018

(30) Foreign Application Priority Data

Jul. 16, 2014 (JP) ................................ 2014-145548

(51) Int. Cl.
G01N 29/265 (2006.01)
A61B 8/00 (2006.01)
(Continued)

(52) U.S. Cl.
CPC ......... *G01N 29/265* (2013.01); *A61B 8/4461* (2013.01); *A61B 8/483* (2013.01);
(Continued)

(58) Field of Classification Search
CPC .......... G01N 29/265; A61B 8/00; A61B 8/14; A61B 8/4263; A61B 8/4483
(Continued)

(56) References Cited

U.S. PATENT DOCUMENTS 3,814,358 A * 6/1974 Sloyan ...................... F16H 3/00
248/655
7,554,245 B2 * 6/2009 Hasegawa ............ G01N 29/265
310/334
(Continued)

FOREIGN PATENT DOCUMENTS

CN 101112321 1/2008
JP H01224563 9/1989
(Continued)

OTHER PUBLICATIONS

Translation JP-11123193-A (Year: 2011).*
(Continued)

*Primary Examiner* — Natalie Huls
*Assistant Examiner* — Monica S Young
(74) *Attorney, Agent, or Firm* — JCIPRNET (57) ABSTRACT An ultrasonic transducer includes a housing, a driving device, and a detecting device. The housing internally includes an ultrasound transmitting/receiving unit, the housing sealing ultrasonic propagation liquid. The driving device includes a driving motor and an intermediate member. The driving device is configured to transmit a rotary driving force from the driving motor to swing the ultrasound transmitting/receiving unit. The detecting device includes a detecting member and is configured to detect an origin position serving as a reference in control of the swing of the ultrasound transmitting/receiving unit. The driving device is configured to transmit the rotary driving force to the intermediate member, extract a rotation of the intermediate
(Continued)

member, decelerate the rotation of the intermediate member and transmit the rotation to the detecting member thereof in a route different from the driving device, and detect the rotation of the detecting member by a sensor to detect an origin position.

5 Claims, 8 Drawing Sheets

(51) Int. Cl.
*A61B 8/08* (2006.01)
*G01N 29/22* (2006.01)
*A61B 8/14* (2006.01)

(52) U.S. Cl.
CPC .............. *G01N 29/225* (2013.01); *A61B 8/14* (2013.01); *A61B 8/4263* (2013.01); *A61B 8/4483* (2013.01); *G01N 2291/02475* (2013.01)

(58) Field of Classification Search
USPC .......................................................... 73/621
See application file for complete search history.

(56) References Cited

U.S. PATENT DOCUMENTS

| | | | |
|---|---|---|---|
| 2006/0284086 A1* | 12/2006 | Hasegawa | G01N 29/265 250/309 |
| 2008/0027326 A1 | 1/2008 | Hasegawa | |
| 2010/0076316 A1* | 3/2010 | Hasegawa | G01N 29/06 600/459 |
| 2013/0207517 A1* | 8/2013 | Naka | G01N 29/24 310/334 |

FOREIGN PATENT DOCUMENTS

| | | | |
|---|---|---|---|
| JP | H0773576 | | 8/1995 |
| JP | 11123193 A | * | 5/1999 |
| JP | H11123193 | | 5/1999 |
| JP | 2006346125 | | 12/2006 |
| JP | 4584321 | | 11/2010 |

OTHER PUBLICATIONS

"International Search Report (Form PCT/ISA/210)", dated Oct. 6, 2015, with English translation thereof, pp. 1-4.
"Office Action of China Counterpart Application," dated Jan. 30, 2019, with English translation thereof, p. 1-p. 14.

* cited by examiner

MECHANICAL SCANNING 3D ULTRASONIC TRANSDUCER

CROSS-REFERENCE TO RELATED APPLICATION

This application is a 371 of international application of PCT application serial no. PCT/JP2015/069842, filed on Jul. 10, 2015, which claims the priority benefits of Japan application no. 2014-145548, filed on Jul. 16, 2014. The entirety of each of the abovementioned patent applications is hereby incorporated by reference herein and made a part of this specification.

TECHNICAL FIELD

The present invention relates to a mechanical scanning 3D ultrasonic transducer. The present invention especially relates to a mechanical scanning 3D ultrasonic transducer that includes a detecting device to detect an origin position serving as a reference in control of a swing of an ultrasound transmitting/receiving unit of the mechanical scanning 3D ultrasonic transducer.

BACKGROUND ART

A conventional mechanical scanning 3D ultrasonic transducer, for example, an arc-shaped scan ultrasonic transducer, which swings an ultrasound transmitting/receiving unit of the ultrasonic transducer in a short-axis direction, includes a rotating disk (an optical rotating plate) at a driving member disposed in the middle of a mechanism to transmit a rotation of a drive motor shaft to the ultrasound transmitting/receiving unit. The mechanical scanning 3D ultrasonic transducer uses a transmission type photosensor to detect a rotation position of the ultrasound transmitting/receiving unit.

Figure 5A:
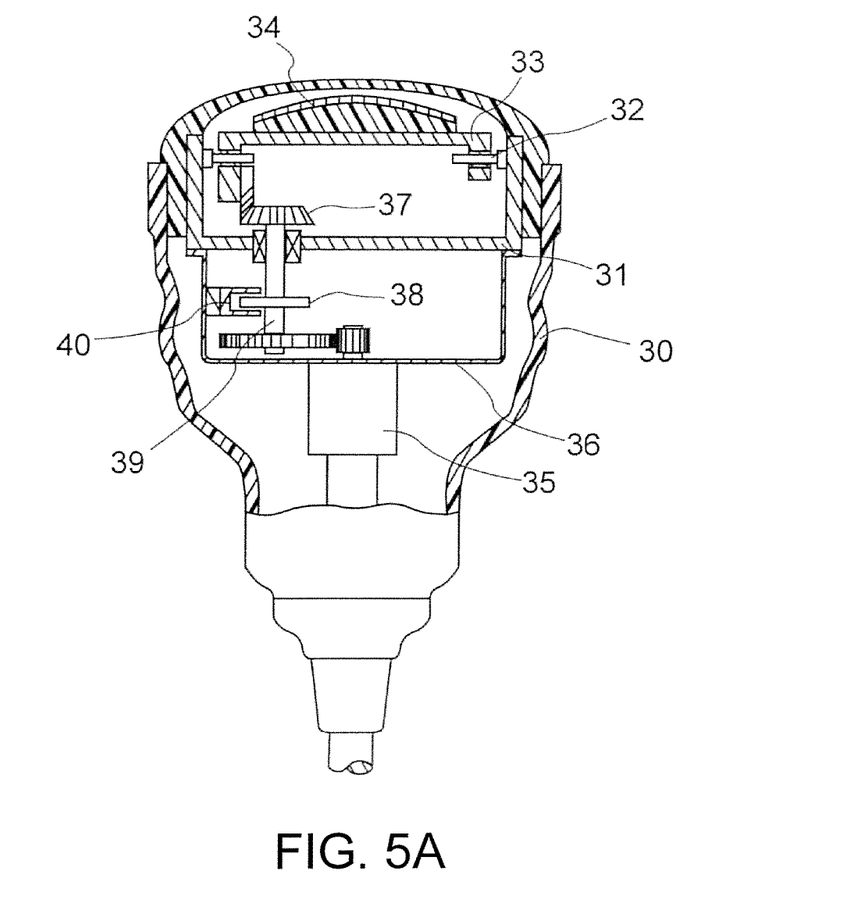
FIG. 5A is a vertical cross-sectional view of a conventional arc-shaped scan type mechanical scanning 3D ultrasonic transducer.

For example, as illustrated in FIG. 5A, a drawing of the conventional arc-shaped scan ultrasonic transducer, the arc-shaped scan ultrasonic transducer includes a case 31 in a housing 30. Holding plates 33 are disposed at both sidewalls on the case 31 to be freely swung by central axes 32. An ultrasound transmitting/receiving unit 34 constituted of a piezoelectric element group is disposed on a top surface portion of the holding plates 33.

A framing body 36 is fixedly secured to a lower surface portion of the case 31. A driving motor 35 is disposed on a lower surface of the framing body 36. A control shaft 39 is connected to a bevel gear mechanism 37, which is disposed inside the case 31, via a gear mechanism. The driving motor 35 causes the control shaft 39 to mesh with a bevel gear fixedly secured to one sidewall of the holding plate 33 to rotate the control shaft 39. Thus, the ultrasound transmitting/receiving unit 34 is swung in the short-axis direction.

Figure 5B:
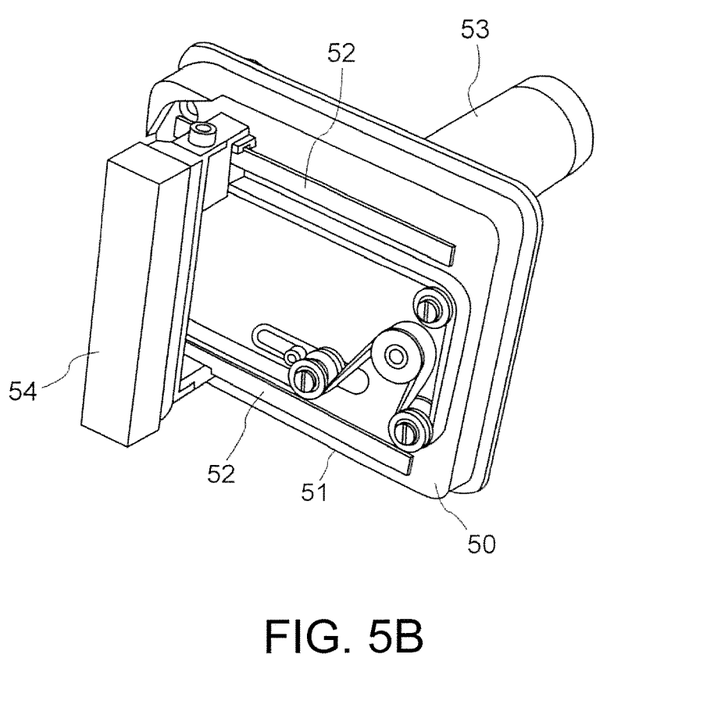
FIG. 5B is a perspective view of a transducer moving mechanism of the linear scan type mechanical scanning 3D ultrasonic transducer.
Figure 5C:
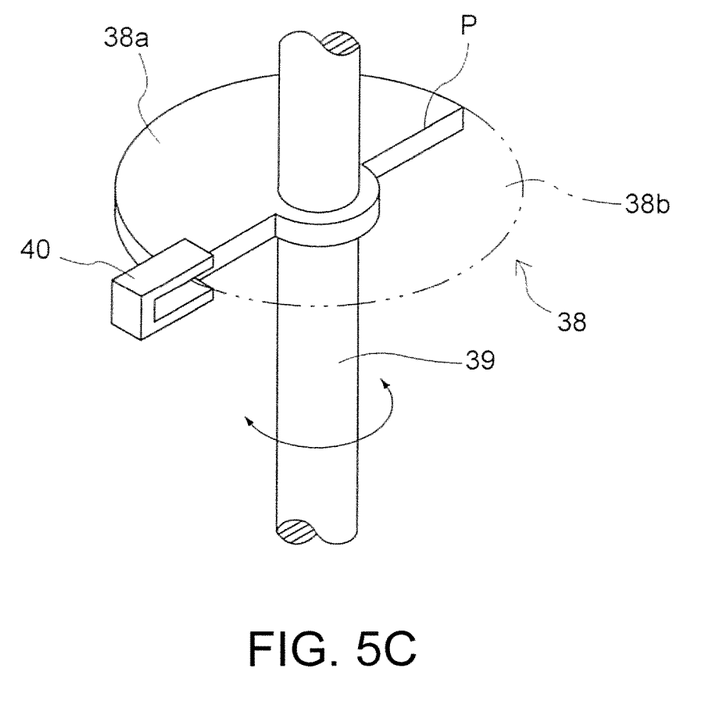
FIG. 5C is an enlarged perspective view of a transmission type photosensor of the arc-shaped scan type mechanical scanning 3D ultrasonic transducer illustrated in FIG. 5A.

As details are illustrated in FIG. 5C, a semilunar optical rotating plate 38 is connected to the control shaft 39 illustrated in FIG. 5A. A light shielding unit 38a and a light transmitting unit 38b are each formed at an interval of 180° in a direction opposite from one another from a rotational center of the optical rotating plate 38 with a boundary P as the reference.

A transmission type photosensor 40 is disposed on an internal surface of the framing body 36. The transmission type photosensor 40 detects an origin position of the ultrasound transmitting/receiving unit 34 in the short-axis direction to ensure obtaining biological information from an accurate position of a subject (a living body) (see Patent Document 1).

A linear scan ultrasonic transducer that reciprocates the ultrasound transmitting/receiving unit of the ultrasonic transducer illustrated in FIG. 5B in a direction parallel to a short-axis direction includes a moving mechanism 51. The moving mechanism 51, which is disposed on a side surface portion of a container body 50, is constituted of a timing belt and a drive pulley. The moving mechanism 51 is guided by a pair of linear guides 52, which are disposed at side surface portions of the container body 50, rotatably drives an electric motor 53, and reciprocates a transducer body (an ultrasonic transducer) 54 in the short-axis direction to perform a linear scan.

The linear scan ultrasonic transducer also swings the ultrasound transmitting/receiving unit in the short-axis direction to cause the ultrasound transmitting/receiving unit to perform the scan. Similar to the arc-shaped scan ultrasonic transducer, a transmission type photosensor (not illustrated) detects a right end portion (an R end) and a left end portion (an L end) in the movement of the ultrasound transmitting/receiving unit in the short-axis direction and detects an origin position to form a two-dimensional image of a subject. Subsequently, the linear scan ultrasonic transducer moves the ultrasound transmitting/receiving unit in the short-axis direction to form a three-dimensional image combined with this two-dimensional image. Thus, biological information can be obtained from an accurate position of the subject (the living body) (see Patent Document 2).

CITATION LIST

Patent Document

Patent Document 1: Japanese Unexamined Patent Application Publication No. 2006-346125
Patent Document 2: Japanese Patent No. 4584321

SUMMARY

Problems to be Solved

Usually, in the case where a visual filed of a subject by ultrasonic diagnostic device is attempted to be widen during diagnosis, increasing an amount of swing of the ultrasound transmitting/receiving unit is necessary. However, if the amount of swing is attempted to be widen by the above-described conventional origin detection method, as illustrated in FIG. 6, the rotating disk possibly rotates by one rotation or more in full stroke.

Figure 6:
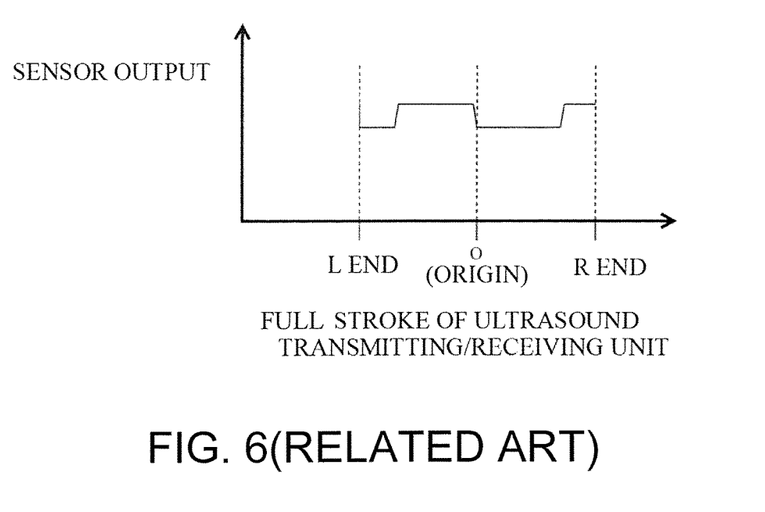
FIG. 6 is a graph illustrating sensor outputs at L end, origin, and R end positions of the transducer in full stroke of by a conventional reducer.

FIG. 6 employs a linear scan ultrasonic transducer where a semilunar circular plate 38 is mounted to the drive shaft (the control shaft 39) described in the above-described Patent Document 1. In FIG. 6, the vertical axis indicates a sensor output from the transmission type photosensor, and the horizontal axis indicates detecting positions, the L end, the origin, and the R end of the ultrasound transmitting/receiving unit in full stroke.

Thus, in the case of FIG. 6, as illustrated in FIG. 5C described above, to detect the origin, a rotation angle range of the optical rotating plate 38 is divided into two, namely two of a light shielding state and a transmitting state of the transmission type photosensor, and the boundary P between the light shielding state and the transmitting state is detected and determined as the origin. Therefore, provisionally, rotating the optical rotating plate 38 by one rotation or more in full stroke detects the origin position twice or more while the ultrasound transmitting/receiving unit is driven in full stroke, from the R end to the L end (as illustrated in FIG. 6, the low sensor output is detected as the origin position). This causes an inconvenience of inaccurate origin detection.

While the ultrasound transmitting/receiving unit stops, whether the ultrasound transmitting/receiving unit is positioned on the L end side or the R end with respect to the origin is determined through detection of the output from the transmission type photosensor, thus deciding an initial driving direction in the origin detection. Therefore, the conventional configuration that rotates the optical rotating plate 38 by one rotation or more in full stroke cannot unambiguously determine the output from the transmission type photosensor relative to the position of the ultrasound transmitting/receiving unit. This causes an inconvenience of failing to determine the movement direction of the ultrasound transmitting/receiving unit.

As countermeasure against such problem, the following is considered. A reduction gear ratio R1 of a rotation speed from the driving motor to an intermediate member is increased. A reduction gear ratio R2 from the intermediate member to the ultrasound transmitting/receiving unit is reduced. Thus, the total rotation speed of the intermediate member is reduced.

However, this deceleration method reduces R2. Therefore, it is indispensable for a mechanism of the prior example that uses large/small bevel gears to swing the ultrasound transmitting/receiving unit to increase a size of the small gear. For example, this increases a size of a liquid chamber in the framing body 36 for sealing ultrasonic propagation liquid in the housing 30, which is illustrated in FIG. 5A. This hinders downsizing and weight reduction of the ultrasonic transducer. On the contrary, it is also considered to reduce a size of the large gear among the bevel gears. However, in terms of a restriction on a bearing mechanism for swinging the ultrasound transmitting/receiving unit (see a central axis 32 in FIG. 5A), it is extremely difficult to reduce the size of the large gear.

Solutions to the Problems

To solve the above-described problems, an ultrasonic transducer of the present invention includes a housing, a driving device, and a detecting device. The housing internally includes an ultrasound transmitting/receiving unit. The housing seals ultrasonic propagation liquid. The driving device is configured to transmit a rotary driving force from a driving motor to swing the ultrasound transmitting/receiving unit. The detecting device is configured to detect an origin position serving as a reference in control of the swing of the ultrasound transmitting/receiving unit. The driving device is configured to transmit the rotary driving force to an intermediate member. The detecting device is configured to extract a rotation from the intermediate member. The detecting device is configured to decelerate the rotation and transmit the rotation to a detecting member thereof. The detecting device is configured to detect the rotation of the detecting member by a sensor to detect an origin position.

The ultrasonic transducer of the present invention is configured as follows. A whole rotation range of the detecting member is divided into two regions of different output states from the sensor. A boundary between the two regions is detected as the origin position.

Furthermore, with the ultrasonic transducer of the present invention, even when the ultrasound transmitting/receiving unit is driven in full stroke, a reduction gear ratio of the detecting member is set such that a total rotation speed of the detecting member becomes one rotation or less.

Furthermore, a driven gear is meshed with a driving gear disposed at the intermediate member to extract the rotation. The driven gear is configured to rotate the detecting member directly or via another linked member.

Furthermore, the driven gear is supported to be relatively movable in a direction that a shaft-to-shaft distance with the driving gear changes. The driven gear and the driving gear are elastically urged in a direction that the driven gear and the driving gear mesh with one another.

Technical Effects

An origin position serving as a reference for control of a swing of an ultrasound transmitting/receiving unit of a mechanical scanning 3D ultrasonic transducer is accurately detected and more accurate three-dimensional image is formed.

DESCRIPTION OF EMBODIMENTS

The following describes embodiments of a mechanical scanning 3D ultrasonic transducer of this application with reference to the accompanying drawings.

Figure 1:
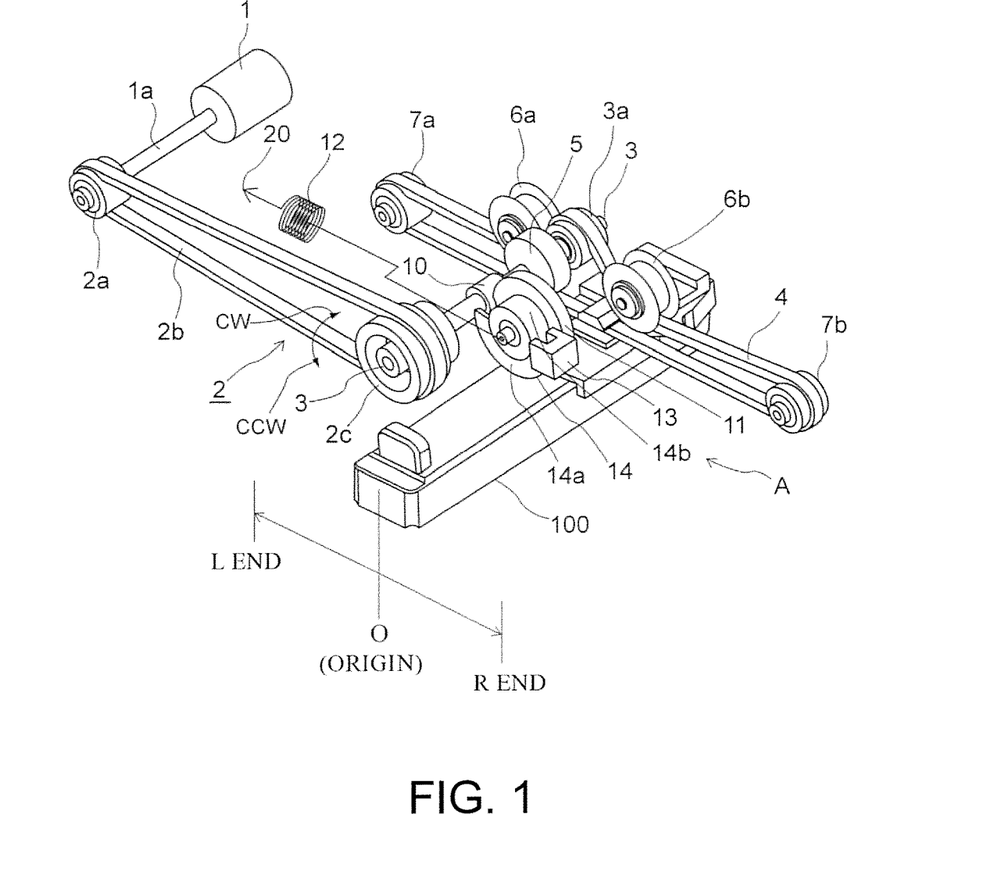
FIG. 1 is a perspective view viewing a driving device and a detecting device according to a first embodiment of a mechanical scanning 3D ultrasonic transducer of this application, especially a linear scan type mechanical scanning 3D ultrasonic transducer from obliquely upward.
Figure 2:
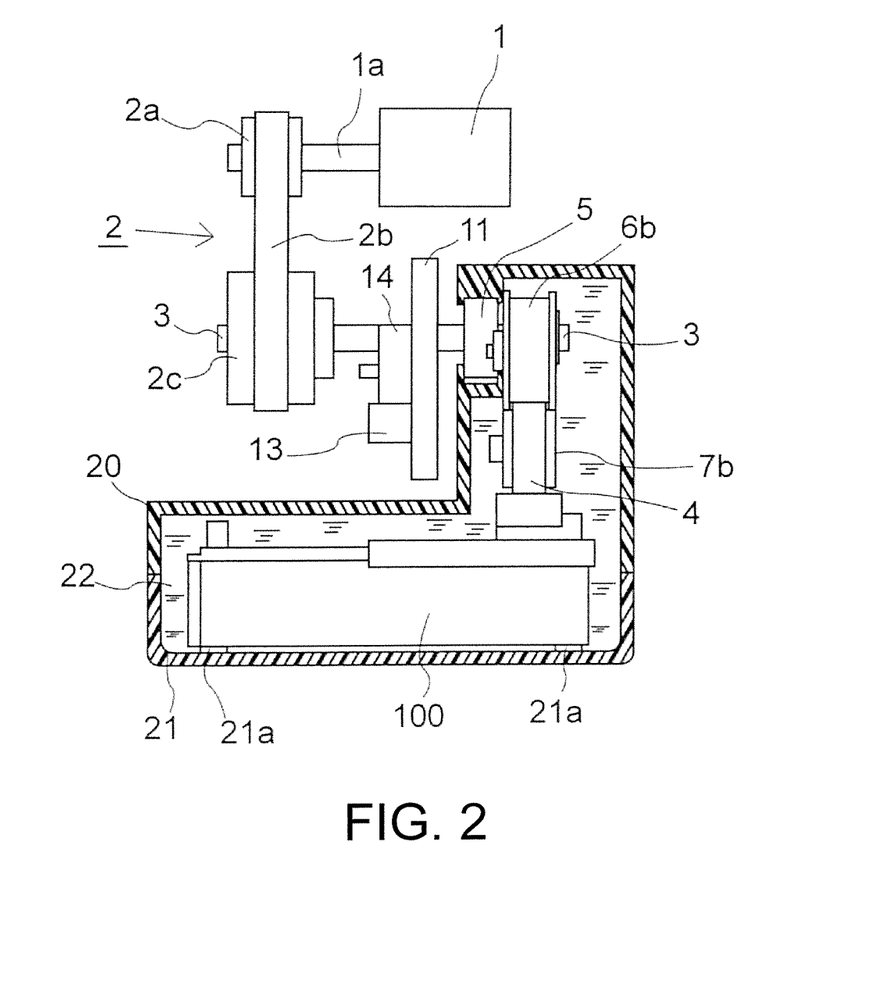
FIG. 2 is a cut arrow view illustrating a base and a housing of the linear scan type mechanical scanning 3D ultrasonic transducer illustrated in FIG. 1 and viewing the illustration from a direction A.

As illustrated in FIG. 1 and FIG. 2, with a first embodiment that applies a mechanical scanning 3D ultrasonic transducer of the present invention to a linear scan type mechanical scanning 3D ultrasonic transducer, a swing (reciprocating) mechanism for an ultrasound transmitting/receiving unit (a transducer body) 100 in a short-axis direction includes a driving motor 1 and a reducer 2. The reducer 2 rotatably drives a drive shaft 3, which transmits this rotary driving force to the ultrasound transmitting/receiving unit 100. As illustrated in FIG. 1, this reducer 2 includes a small pulley 2a, a large pulley 2c, and a first timing belt 2b. The small pulley 2a and the large pulley 2c are fixedly secured to an output shaft 1a of the driving motor 1, which is journaled to a base 20 illustrated in FIG. 2. The first timing belt 2b is suspended between both of the pulleys 2a and 2c.

As illustrated in FIG. 2, the drive shaft 3 is journaled to the base 20 via an oil seal 5. The first timing belt 2b, which is suspended between both of the pulleys 2a and 2c, decelerates and transmits a rotation of the small pulley 2a, which is fixedly secured to the output shaft 1a of the driving motor 1, to the large pulley 2c to rotate the drive shaft 3, which journals the large pulley 2c at its one end portion, clockwise (CW) and counterclockwise (CCW).

This configuration drives a second timing belt 4 in the L end and R end directions in alternation. The second timing belt 4 is in contact with an outer peripheral portion of a drive shaft pulley 3a journaled to the other end portion of the drive shaft 3. Additionally, the second timing belt 4 is laid across in a tensioned state between first and second idle pulleys 7a and 7b, which are disposed on respective sidewalls of the base 20 at swing end portions in the short-axis direction equivalent to the L end and the R end of the ultrasound transmitting/receiving unit (the transducer body) 100. A first tension pulley 6a and a second tension pulley 6b provide tension to the second timing belt 4.

The driving of this second timing belt 4 causes the ultrasound transmitting/receiving unit 100 to be guided by a pair of parallel guide mechanisms 21a (see the linear guides 52 illustrated in FIG. 5, the drawing for the prior example), which are laid on an inner bottom surface of the housing 21. Thus, the ultrasound transmitting/receiving unit 100 linearly moves in the short-axis direction (The rotation of the drive shaft 3 in the CW direction illustrated in FIG. 1 moves the ultrasound transmitting/receiving unit 100 in the L end direction. The rotation of the drive shaft 3 in the CCW direction moves the ultrasound transmitting/receiving unit 100 in the R end direction).

Additionally, as illustrated in FIG. 1, a driving gear 10 is disposed at an intermediate position between both right and left ends of the drive shaft 3. This driving gear 10 is meshed with a driven gear 11 with the larger number of tooth compared with those of this driving gear 10. This branches the rotation speed of the drive shaft 3 from the middle of the drive system to decelerate the drive shaft 3 and rotate a rotating disk 14 disposed integrally with the driven gear 11. Similar to the optical rotating plate illustrated in FIG. 5C, a boundary P between a light shielding unit 14a and a light transmitting unit 14b is detected to detect an origin position O.

The movement of the ultrasound transmitting/receiving unit 100 in the R end direction rotates the rotating disk (the detecting member) 14 in the CW direction illustrated in FIG. 1. The movement of the ultrasound transmitting/receiving unit 100 in the L end direction rotates the rotating disk 14 in the CCW direction.

Furthermore, a presence of so-called backlash at a mesh portion where the driving gear 10 meshes with the driven gear 11 generates an error in a timing at which the ultrasound transmitting/receiving unit 100 passes through the preset origin position during the swing and a timing at which the sensor output from the rotating disk 14 changes. In the case where the movement (the swing) directions of the ultrasound transmitting/receiving unit 100 are opposite, that is, the case of the movement from the L end to the R end direction and the case of the movement from the R end to the L end direction, this timing error is remarkable. This causes a problem to form a three-dimensional image of a subject by an ultrasonic diagnostic device.

To solve this problem, as illustrated in FIG. 1, the linear scan type mechanical scanning 3D ultrasonic transducer of the present invention is configured as follows. A holding member (not illustrated) supports the above-described driven gear 11 such that a shaft distance with the driving gear 10 can be freely changed. The base 20 supports the one end of the driven gear 11. A helical spring 12 mounted to the driven gear 11 always urges the other end of the driven gear 11 in a direction of the driving gear 10.

The urging by this helical spring 12 allows almost zeroing the backlash generated between the driving gear 10 and the driven gear 11. It is only necessary that the rotating disk (the detecting member) 14 be secured to the above-described holding member (not illustrated) for the driven gear 11. Accordingly, compared with the case of disposing another rotating disk 14, this achieves a reduction in size of the ultrasonic transducer and in production cost.

As illustrated in FIG. 2, especially, the oil seal 5 seals and supports the drive shaft 3 to the base 20. Therefore, this does not leak ultrasonic propagation liquid 22 such as oil sealed in the housing 21 from the base 20 and the housing 21.

Additionally, as illustrated in FIG. 1, the second timing belt 4 is laid across in the tensioned state between the first and the second idle pulleys 7a and 7b, which are disposed on the respective sidewalls of the base 20 at the swing end portions in the short-axis direction equivalent to the L end and the R end of the ultrasound transmitting/receiving unit 100. The first tension pulley 6a and the second tension pulley 6b provide tension to the second timing belt 4, and the second timing belt 4 is laid by being extended to the base 20 and the inside of the housing 21.

A spring (not illustrated) may urge any one of the first tension pulley 6a and the second tension pulley 6b to appropriately provide the tension to the second timing belt 4. Alternatively, the spring may urge the first and the second idle pulleys 7a and 7b to provide the tension to the second timing belt 4.

As described above, the mechanical scanning 3D ultrasonic transducer of the present invention employs the reducer with the timing belt, the pulleys, and the gear mechanism, instead of the conventional reducer using a spur gear or the bevel gear for all decelerations as illustrated in FIG. 5A. This ensures substantially increasing the reduction gear ratio from the driving motor to the drive shaft. Additionally, the combination of the driving gear and the driven gear substantially decelerates the total rotation speed of the rotating disk, which constitutes the transmission type photosensor, in full stroke.

Consequently, as described later, the total rotation speed of the rotating disk can be decelerated to one rotation or less in full stroke.

Figure 3:
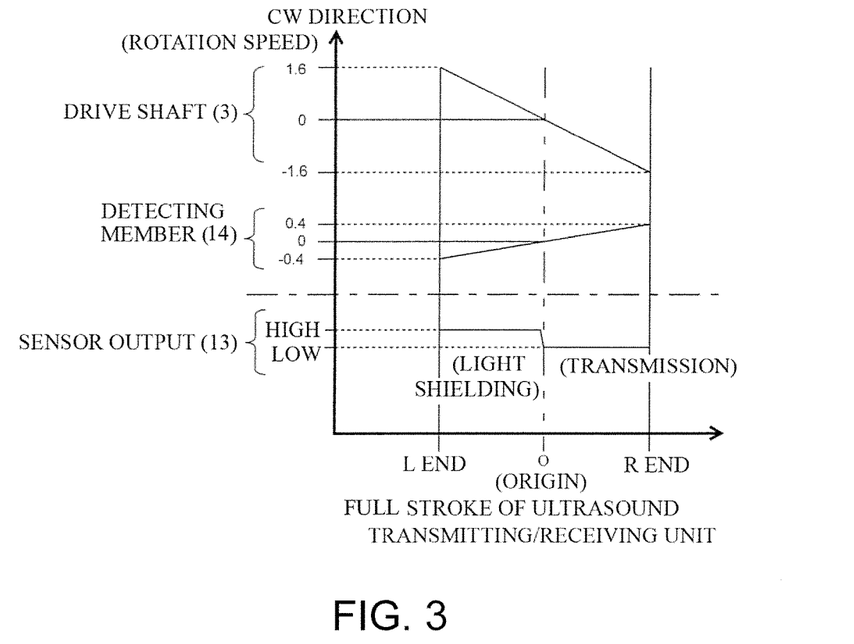
FIG. 3 is a graph illustrating clockwise rotation speeds of the drive shaft and the detecting member and level of a sensor output at L end, origin, and R end positions of the mechanical scanning 3D ultrasonic transducer according to this application in full stroke.

That is, as illustrated in FIG. 3, the horizontal axis indicates the full stroke of the ultrasound transmitting/receiving unit. The vertical axis indicates the clockwise rotation speeds of the drive shaft 3 and the detecting member (the rotating disk) 14 and the output from the transmission type photosensor 13. FIG. 3 plots and graphs these rotation speeds and the sensor output of the ultrasound transmitting/receiving unit 100 from the L end to the R end through an origin O.

According to this graph (FIG. 3), when the ultrasound transmitting/receiving unit 100 moves from the L end to the R end, the full stroke, the drive shaft 3 rotates by ±1.6; therefore, the total rotation speed becomes 3.2 rotations. However, with Embodiment 1 of the mechanical scanning 3D ultrasonic transducer of the present invention, the rotating disk 14 is decelerated to one-quarter of the rotation speed of the drive shaft 3 by the reduction gear ratio between the driving gear 10 and the driven gear 11. Accordingly, the rotating disk 14 rotates by only ±0.4. Eventually, the total rotation speed of the rotating disk 14 becomes the rotation speed of 0.8, namely, one rotation or less in full stroke. This does not cause the error in the origin position O of the ultrasound transmitting/receiving unit 100.

Embodiment 1 of the mechanical scanning 3D ultrasonic transducer of the present invention uses the transmission type photosensor to detect the origin. However, this should not be construed in a limiting sense. A reflective photo sensor, a magnetic detection sensor, a contact type brush encoder, or a similar device may be employed.

Figure 4:
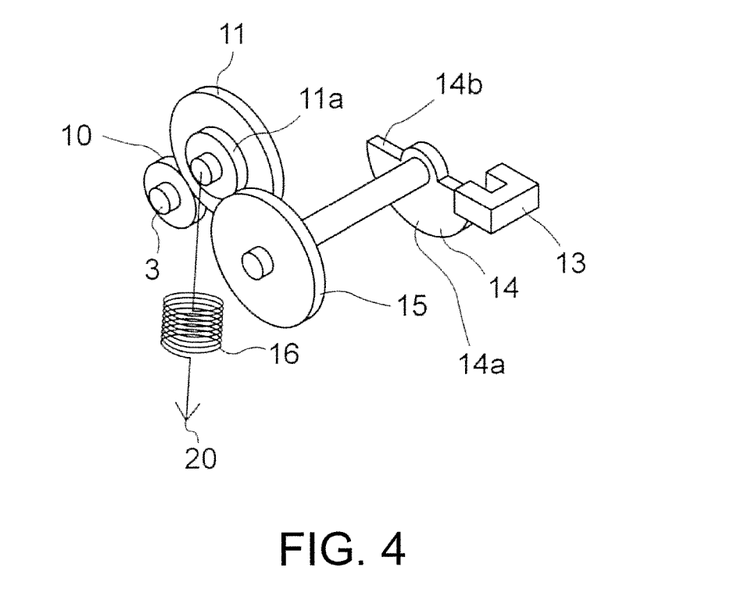
FIG. 4 is a block diagram of a second embodiment of a reducer illustrated in FIG. 1.

The above-described first embodiment of the present invention meshes the one driving gear with the one driven gear for deceleration of the rotating disk. However, as illustrated in FIG. 4, a second embodiment of the present invention further includes a second driven gear 15 at the subsequent stage of the first driven gear 11 of the above-described first embodiment. This embodiment meshes the second driven gear 15 with a small gear 11a formed concentrically with the first driven gear 11 to obtain a greater reduction gear ratio.

This second embodiment supports the first driven gear 11 such that both of the shaft distances between the first driven gear 11 and the driving gear 10 and the second driven gear 15 can be changed. Additionally, a second tension spring 16 urges the first driven gear 11 in a direction where the first driven gear 11 meshes with both of the meshing gears. This ensures eliminating the backlash while the respective driving gears mesh with one another at the same time.

Accordingly, the second embodiment of the present invention allows obtaining the reduction gear ratio larger than that of the above-described first embodiment. Additionally, even with the reduction gear ratio equivalent to the first embodiment, diameters of the respective large driving gears can be reduced. Therefore, even if a layout of the ultrasonic transducer is restricted, the freedom of design is extremely high.

The ultrasonic transducer of the present invention is also applicable to the arc-shaped scan type mechanical scanning 3D ultrasonic transducer. The ultrasonic transducer is more effectively applicable to the linear scan type mechanical scanning 3D ultrasonic transducer, which requires much amount of driving (amount of movement) for the ultrasound transmitting/receiving unit.

The invention claimed is:

1. An ultrasonic transducer, comprising:
a housing that internally includes an ultrasound transmitting/receiving unit, and the housing sealing an ultrasonic propagation liquid;
a driving device that includes a driving motor and a drive shaft which is an intermediate member rotationally driven by the driving motor, the driving device being configured to transmit a rotary driving force from the driving motor to swing the ultrasound transmitting/receiving unit; and
a detecting device that includes a detecting member and is configured to detect an origin position serving as a reference in control of a swing of the ultrasound transmitting/receiving unit, wherein
the driving device is configured to transmit the rotary driving force to the intermediate member,
the drive shaft is disposed such that one end portion of the drive shaft enters an interior of the housing and transmits the rotary driving force to the interior of the housing,
the detecting device being configured to extract a rotation of the intermediate member outside of the housing, a reduction element being configured to decelerate the rotation of the intermediate member and transmit the rotation which is decelerated to the detecting member of the detecting device in a route different from the driving device, and the detecting member is rotated at a first rotation speed lower than a second rotation speed of the drive shaft, and the detecting device being configured to detect the rotation of the detecting member by a sensor to detect an origin position.

2. The ultrasonic transducer according to claim 1, wherein
a whole rotation range of the detecting member is divided into two regions of different output states from the sensor, and
a boundary between the two regions is detected as the origin position, and
even when the ultrasound transmitting/receiving unit is driven in full stroke, a reduction gear ratio of the detecting member is set such that a total rotation speed of the detecting member becomes one rotation or less.

3. The ultrasonic transducer according to claim 1, wherein
a driven gear is meshed with a driving gear disposed at the drive shaft to extract the rotation, and
the driven gear is configured to rotate the detecting member directly or via another linked member.

4. The ultrasonic transducer according to claim 3, wherein
the driven gear is supported to be relatively movable with respect to the drive gear in a direction that a shaft distance between a shaft of the driven gear and a shaft of the driving gear changes, and
the driven gear and the driving gear are elastically urged in a direction that the driven gear and the driving gear mesh with one another.

5. The ultrasonic transducer according to claim 3, wherein
a first driven gear is meshed with the driving gear disposed at the drive shaft to extract the rotation, and
the first driven gear rotates the detecting member via a second driven gear meshed with a small gear formed coaxially with the first driven gear, and
the first driven gear is supported to be relatively movable with respect to both of the driving gear and the second driven gear in a direction that, each shaft distance between a shaft of the driving gear and a shaft of the first driven gear, and between a shaft of the first driven gear and a shaft of the second driven gear changes, and
the first driven gear is elastically urged in a direction that the first driven gear is meshed with both of the driving gear and the second driven gear.

* * * * *